(12) United States Patent
Wang et al.

(10) Patent No.: US 11,135,053 B2
(45) Date of Patent: Oct. 5, 2021

(54) IMPLANTATION METHOD OF ARTIFICIAL HEART VALVE

(71) Applicant: LIFETECH SCIENTIFIC (SHENZHEN) CO., LTD, Shenzhen (CN)

(72) Inventors: Zhiwei Wang, Shenzhen (CN); Jianzhou Guo, Shenzhen (CN); Wenbin Chen, Shenzhen (CN); Wei Jiang, Shenzhen (CN); Huixiong Xie, Shenzhen (CN); Xiangdong Liu, Shenzhen (CN); Bin Yao, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 180 days.

(21) Appl. No.: 16/223,480

(22) Filed: Dec. 18, 2018

(65) Prior Publication Data

US 2020/0188093 A1    Jun. 18, 2020

(51) Int. Cl.
*A61F 2/24* (2006.01)

(52) U.S. Cl.
CPC .......... *A61F 2/2412* (2013.01); *A61F 2/2433* (2013.01); *A61F 2/2454* (2013.01); *A61F 2/2466* (2013.01); *A61F 2220/0075* (2013.01)

(58) Field of Classification Search
CPC ..... A61F 2/2433; A61F 2/2466; A61M 25/09; A61M 25/09008; A61M 25/09175
See application file for complete search history.

(56) References Cited

U.S. PATENT DOCUMENTS

| | | | | |
|---|---|---|---|---|
| 2007/0027534 | A1* | 2/2007 | Bergheim | A61F 2/013 623/2.11 |
| 2011/0029071 | A1* | 2/2011 | Zlotnick | A61B 17/00234 623/2.11 |
| 2012/0310330 | A1* | 12/2012 | Buchbinder | A61M 25/1011 623/2.11 |
| 2014/0114404 | A1* | 4/2014 | Gammie | A61F 2/2457 623/2.11 |
| 2014/0303719 | A1* | 10/2014 | Cox | A61F 2/2466 623/2.11 |
| 2014/0371846 | A1* | 12/2014 | Wilson | A61F 2/24 623/2.11 |
| 2017/0056169 | A1* | 3/2017 | Johnson | A61F 2/2436 |
| 2017/0079790 | A1* | 3/2017 | Vidlund | A61F 2/2418 |
| 2018/0125642 | A1* | 5/2018 | White | A61F 2/243 |

* cited by examiner

*Primary Examiner* — Alexander J Orkin
(74) *Attorney, Agent, or Firm* — Maier & Maier, PLLC (57) ABSTRACT

The present application provides an implantation method of an artificial heart valve. The implantation method can include forming an incision in the left chest to expose the ventricle; advancing a guide wire kept away from chordae tendineaes through the atrium into the ventricle; advancing a guide wire catcher into the ventricle from the incision to pull out the distal end of the guide wire from the ventricle; and advancing the artificial heart valve into the ventricle from the distal end of the guide wire with a valve deliverer, and placing the artificial heart valve at a primary valve between the ventricle and the atrium along the guide wire. The artificial heart valve may avoid the chordae tendineaes in the heart system through the guide wire track during implantation.

10 Claims, 11 Drawing Sheets

IMPLANTATION METHOD OF ARTIFICIAL HEART VALVE

FIELD

The present application relates to the technical field of interventional medical devices, and more particularly relates to an implantation method of an artificial heart valve.

BACKGROUND

This part only provides background information related to the present disclosure, and is not necessarily the prior art.

Figure 1:
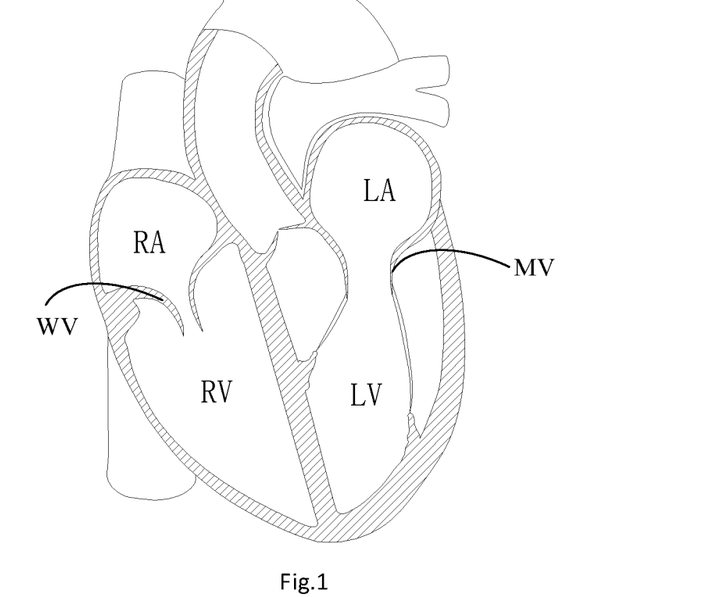
FIG. 1 is a structural schematic diagram of all chambers and a mitral valve in a heart system.

As shown in prior art FIG. 1, the human heart is divided into a left heart system and a right heart system. The left heart system includes a left atrium LA and a left ventricle LV. The right heart system includes a right atrium RA and a right ventricle RV. The left atrium LA, the left ventricle LV, the right atrium RA and the right ventricle RV divide the heart into four chambers. Each chamber has a respective "outlet", and a mitral valve MV, an aortic valve, a pulmonary valve and a tricuspid valve WV are respectively arranged at the respective "outlets". The four valves allow the blood pumped by the heart to be circulated in a cardiovascular system according to an appointed direction. The mitral valve MV is located between the left atrium LA and the left ventricle LV and is connected with the papillary muscle in the left ventricle LV through a chordae tendineae. The normal mitral valve MV allows a certain amount of blood to flow from the left atrium LA to the left ventricle LV in the process of blood circulation. When the left ventricle LV contracts, two flexible flaps of the mitral valve MV close to prevent the backflow of blood from the left ventricle LV into the left atrium LA. However, heart diseases and degenerative changes would cause the dysfunction of the mitral valve MV, and cause the mitral valve MV to become abnormally narrow or leaky, leading to backflow of the blood from the left ventricle LV into the left atrium LA. Therefore, a function and injury of the mitral valve MV may affect the normal work of the heart, gradually debilitating people and even endangering the life of people.

In view of the a function and injury of the mitral valve MV, there have been various therapies and devices for treating mitral valve dysfunction at the present, such as traditional valve replacement known as "heart opening" surgery. In a word, the valve replacement is to open the chest, start extracorporeal circulation with a heart-lung machine, then stop the heart beating and open the heart, and cut away and replace the mitral valve MV of a patient. The complicated operation of the extracorporeal circulation and low tolerance of elder patients give rise to a relatively high medical accident risk of the valve replacement. Therefore, an interventional therapy for the mitral valve MV has gradually drawn attention of people, such as a developed transcatheter technology causing a relatively small trauma to the heart and used for delivering a replacement mitral valve assembly. In this technology, a self-expandable prosthetic valve is generally installed at the tail end of a flexible catheter in a convolved state and is pushed through a blood vessel or the body of a patient till it arrives at an implantation part, and then expands at a defective natural mitral valve to its functional size.

Figure 2:
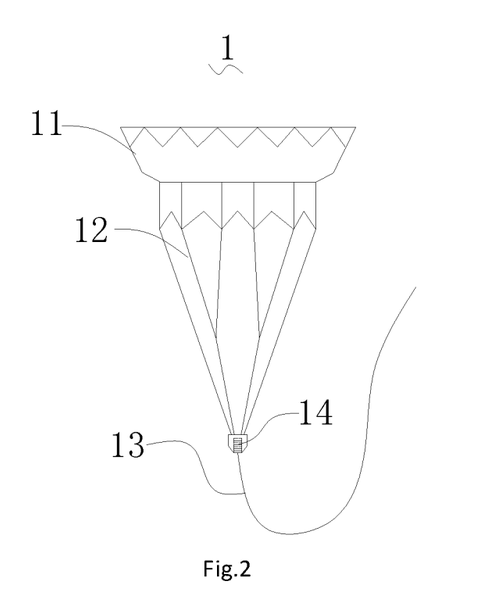
FIG. 2 is a structural schematic diagram of a mitral valve prosthesis.

As shown in prior art FIG. 2, a mitral valve prosthesis 1 includes a valve skirt 11, a valve frame main body 12, a leaflet (not shown in the figure) and a tie rope 13. The outer diameter of the valve skirt 11 is greater than an opening of the mitral valve MV. After the mitral valve prosthesis 1 is implanted into the heart, the valve skirt 11 is located on one side of the left atrium LA, so that the whole mitral valve prosthesis 1 is "located" on a tissue at the opening of the mitral valve and may not fall into the left ventricle LV from one side of the left atrium LA. The valve frame main body 12 is located at a primary mitral valve position, and the tie rope 13 is connected to the distal end of the valve frame main body 12 and is fixed at the cardiac apex position. The mitral valve prosthesis 1 may be stably arranged on the tissue at the opening of the mitral valve, is hard to fall off from a primary mitral valve leaflet and causes little injury to the primary mitral valve leaflet, so that the service life of the mitral valve prosthesis 1 may be prolonged, and the risk of performing secondary valve replacement surgery on the patient is lowered.

Figure 3:
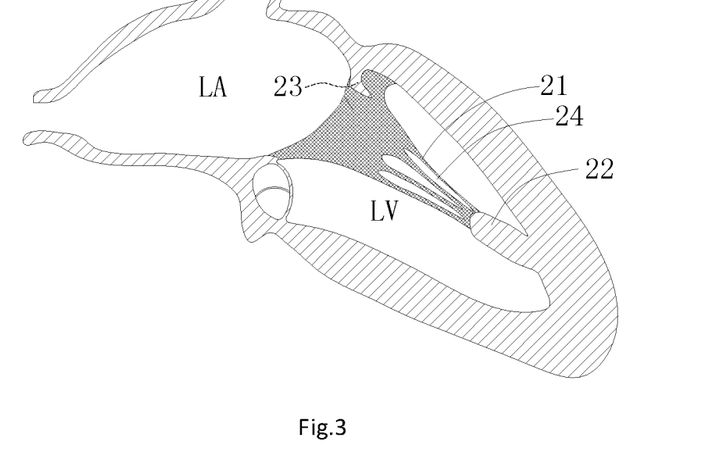
FIG. 3 is an internal structural schematic diagram of the left atrium and the left ventricle.
Figure 4:
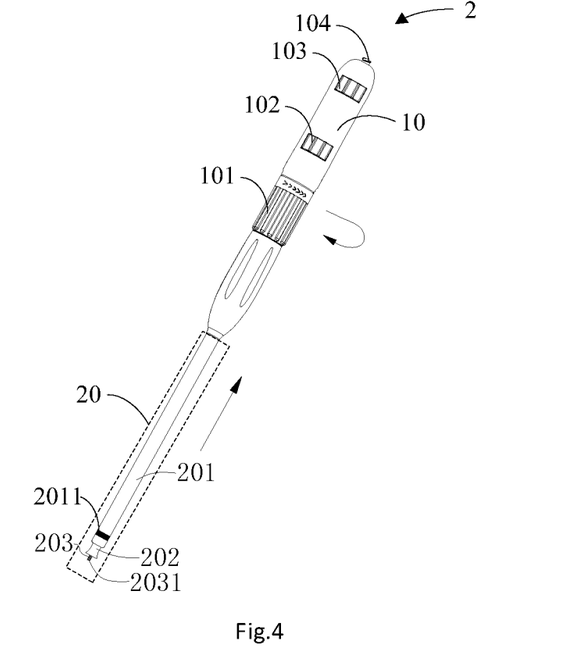
FIG. 4 is a structural schematic diagram of a valve deliverer.
Figure 5:
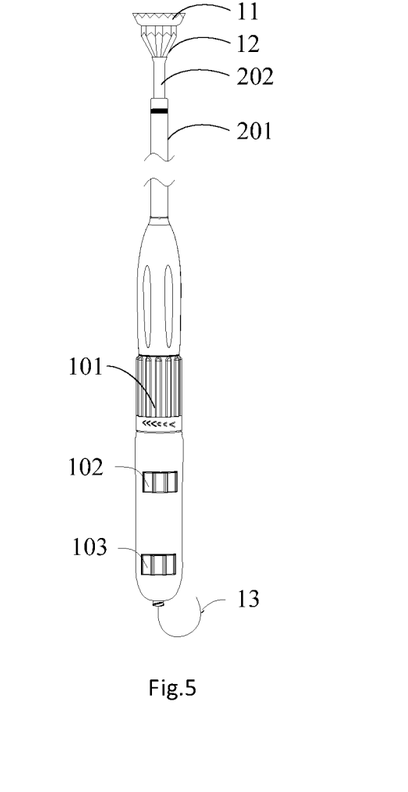
FIG. 5 is an assembled structural schematic diagram of the valve deliverer and the mitral valve prosthesis.

As shown in prior art FIG. 3, two ends of the chordae tendineae 21 in the left ventricle LV are respectively connected with a papillary muscle 22 and a mitral valve leaflet 23. The chordae tendineae 21 and the papillary muscle 22 pull the mitral valve leaflet 23 to keep the mitral valve leaflet 23 from turning towards the left atrium LA, so as to prevent the blood in the left ventricle LV from flowing back into the left atrium LA from the ventricle LV. As the tail end of the mitral valve prosthesis 1 in FIG. 2 is connected with the tie rope 13, and relatively large gaps 24 exist between multiple chordae tendineaes 21 extending out of the same papillary muscle 22, it is very easy for relevant devices to pass through the gaps 24 between the chordae tendineaes 21 during building of an implantation pathway of the mitral valve prosthesis 1, the tie rope 13 also pass through the gaps 24 between the chordae tendineaes 21 after the mitral valve prosthesis 1 is implanted into the opening of the mitral valve MV, and the mitral valve prosthesis 1 may not be horizontally placed at the opening of the mitral valve MV, causing risks of perivalvular leakage and blood backflow of the mitral valve prosthesis 1. In addition, scholarly research in recent years have found that the chordae tendineaes 21 are related to cardiac souffle, arrhythmia, chest pain, chest distress and palpitation; therefore, it is particularly important to build an appropriate implantation pathway for an artificial heart valve 1 to allow the implantation track of the artificial heart valve to bypass the gaps 24 between the chordae tendineaes 21. Furthermore, the appropriate implantation pathway for the artificial heart valve may reduce surgical damage to the chordae tendineaes 21 and may allow the artificial heart valve to be horizontally released at the opening of the mitral valve MV to reduce the occurrence probability of the perivalvular leakage of the artificial heart valve. Therefore, it is necessary to provide a novel implantation method of the artificial heart valve to solve the various problems that the tie rope on the artificial heart valve passes through the gaps 24 between the chordae tendineaes 21 in the existing implantation operation of the artificial heart valve and the tie rope 13 and surgical devices damage the chordae tendineaes 21 in the surgical procedure.

SUMMARY

Exemplary embodiments shown and described in the prevent application provide an implantation method of an artificial heart valve to effectively reduce the phenomenon that the artificial heart valve passes through gaps of chordae tendineaes during implantation on the basis of all of the above problems during implantation of the artificial heart valve in the prior art. The implantation method is mainly implemented through the following technical solutions.

In an exemplary embodiment, the present application provides an implantation method of an artificial heart valve. The implantation method of the artificial heart valve includes: S12: forming an incision in the left chest to expose the ventricle; S14: advancing a guide wire kept away from chordae tendineaes through the atrium to the ventricle; S16: advancing a guide wire catcher into the ventricle from the incision to pull out the distal end of the guide wire from the ventricle; and S18: advancing the artificial heart valve into the ventricle from the distal end of the guide wire with a valve deliverer, and placing the artificial heart valve at a primary valve between the ventricle and the atrium along the guide wire.

According to an exemplary embodiment of the implantation method of the artificial heart valve of the present application, a balloon catheter passes through the atrium and the ventricle in sequence at first, and a balloon on the balloon catheter may reduce the phenomenon that the balloon catheter passes through the gaps between the chordae tendineaes. When the balloon catheter moves to the cardiac apex position of the ventricle, the guide wire is advanced into the cardiac apex of the ventricle through a guide wire channel inside the balloon catheter, and then the guide wire catcher is advanced into the ventricle from the outside of the ventricle to pull the distal end out of the guide wire from the ventricle, so as to build a guide wire track for the artificial heart valve. After the guide wire track for the artificial heart valve is built, the valve delivery delivers the artificial heart valve from the outside of the ventricle to the primary valve between the ventricle and the atrium along the guide wire track. The proximal end of the artificial heart valve is connected with a tie rope, so after the artificial heart valve is implanted to the primary valve of the heart, the valve delivery device pulls the tie rope out of the heart and fixes it at the cardiac apex part on the surface of the heart, and applies a certain pull force to the tie rope to enable the tie rope in the heart to be in a tightened state, and at the moment, the artificial heart valve is clung to a tissue near the opening of the primary valve under the pull force of the tie rope. The tie rope on the artificial heart valve passes through the heart through the guide wire track, so that the phenomenon that the tie rope rubs the chordae tendineaes in the ventricle may be reduced, and the artificial heart valve may be horizontally implanted into the tissue at the opening of the primary valve under the pull force of the tie rope to reduce the phenomenon of the perivalvular leakage during use of the artificial heart valve.

BRIEF DESCRIPTION OF THE DRAWINGS

Those ordinarily skilled in the art can clearly know various other advantages and benefits by reading detailed descriptions of preferred implementation modes below.

Accompanying drawings are merely to show the implementation modes, but are not deemed as limiting the present application. Furthermore, in the whole accompanying drawings, same components are expressed by same reference symbols. In the drawings.

DETAILED DESCRIPTION

Exemplary embodiments of implementation modes of the present disclosure will be described in more details below in combination with accompanying drawings. Although the accompanying drawings show the exemplary implementation modes of the present disclosure, it should be understood that the present disclosure may be implemented in various forms and shall not be limited by the implementation modes described herein. On the contrary, these implementation modes are provided to understand the present disclosure more clearly and completely show the scope of the present disclosure to those skilled in the art. It should be noted that the present application is described by applying an implantation method of an artificial heart valve to implantation surgery of a mitral valve prosthesis, but is not to limit the application scope of the implantation method of the artificial heart valve. For example, the implantation method of the artificial heart valve of the present application may be further applied to the implantation operation of other valve prosthesis in the heart system, such as the implantation operation of a tricuspid valve. This adjustment falls within the protection scope of the implantation method of the artificial heart valve of the present application.

It should be understood that terms used herein is for the purpose of describing specific exemplary implementation modes only and is not intended to be limiting of the exemplary implementation modes. The singular forms "a", "an" and "the" used herein are intended to include the plural forms as well, unless the context clearly indicates otherwise. The terms "include", "comprise", "contain" and "has" are inclusive and thus specify the presence of stated features, steps, operations, elements, and/or components, but do not preclude the presence or addition of one or more other features, steps, operations, elements, components, and/or combinations thereof. Method steps, processes and operations described herein are not explained to be necessarily executed according to a described or stated order, unless an execution order is indicated specifically otherwise. It should be further understood that other or substitutive steps may be used, as desired or as appropriate.

To facilitate the descriptions, the relation between one element or feature as shown in the figure and another element or feature may be described by spatial relation terms used herein. These relation terms, for example, include "inside", "outside", "inner side", "outer side", "under", "below", "over", "above" and the like, which are intended to include different orientations of devices in using or operating in addition to the orientations described in the drawings. For example, if the devices in the drawings turn over, it is described that the elements "under other elements or features" or "below other elements or features" will be then orientated to be "over other elements or features" or "above other elements or features". Therefore, the exemplary term "below . . . " may include upper and lower orientations. The devices may be orientated in other ways (rotating 90 degrees or in other directions), and spatial relation descriptors used herein are correspondingly explained.

It should be noted that in the field of interventional medical devices, the end, closer to an operator, of a medical device implanted into a human body or an animal body is a "proximal end", and the end farther to the operator is a "distal end". The "proximal end" and the "distal end" of any component of the medical device are defined according this principle. The "axial direction" generally means the lengthwise direction of the medical device during delivery, and the "radial direction" generally means a direction perpendicular to the "axial direction" of the medical device. The "axial direction" and the "radial direction" of any component of the medical device are defined according to this principle.

As shown in exemplary FIGS. 4, 5, 8, 10, 13, 16, and 19, exemplary embodiments of the present application can provide an implantation device of an artificial heart valve. The implantation device of the artificial heart valve mainly includes a balloon catheter 321, an operating knife (not shown in the figures), a guide wire catcher (described below in detail) and a valve delivery device 2. The balloon catheter 321 may advance a guide wire 322 passing through the atrium and the ventricle in sequence and kept away from chordae tendineaes 21 into a heart system. The operating knife is used for forming an incision in the left chest to expose the ventricle. The guide wire catcher may be advanced into the ventricle from the incision to pull out the distal end of the guide wire 322 from the ventricle. The valve delivery device 2 may advance the artificial heart valve into the ventricle from the distal end of the guide wire 322 and place it at a primary valve between the ventricle and the atrium along the guide wire 322. The balloon catheter 321 of the present application includes a guide tube. An inflating channel and a guide wire channel are arranged in the guide tube. The distal end of the guide tube is provided with a balloon 3211 communicated with the inflating channel. Further, for the cooperation with the balloon catheter 321 to advance the guide wire 322 passing through the atrium and the ventricle in sequence and kept away from the chordae tendineaes 21 into the heart system, the implantation device of the artificial heart valve of the present application further includes a vascular sheath (not shown in the figures), a puncture sheath 311, a puncture expander 312 and a puncture needle 313. The vascular sheath may puncture an inferior vena cava A. The puncture sheath 311 and the puncture expander 312 may be guided into the right atrium RA through a puncture hole in the inferior vena cava A. The puncture needle 313 may be pushed out from the puncture sheath 311 to puncture the atrial septum between the right atrium RA and the left atrium LA so as to provide a pathway for guiding the balloon catheter 321 into the left atrium LA and the left ventricle LV. The guide wire catcher of the present application includes a cardiac apex puncture needle (not shown in the figures), a guide sheath 331, a catching rod 332 and a contractible ring sleeve 333. The cardiac apex puncture needle is used for puncturing the ventricle. The catching rod 332 may be arranged in the guide sheath 331 in an axial sliding and sleeved manner. The contractible ring sleeve 333 is arranged at the distal end of the catching rod 332. The guide sheath 331 may be guided into the cardiac apex through a cardiac apex puncture hole. The catching rod 332 may be led into the left ventricle LV through the guide sheath 331. The valve delivery device 2 of the present application includes a sheath assembly 20 including an outer sheath catheter 201, a withdrawing catheter 202 and a connecting catheter 203. The outer sheath catheter 201 is used for puncturing the ventricle. The withdrawing catheter 202 is arranged in the outer sheath catheter 201 in an axial sliding and sleeved manner. The connecting catheter 203 is arranged in the withdrawing catheter 202 in a rotatable-sleeved manner. The distal end of the connecting catheter 203 is provided with an advanced rod 2031 in advanced connection with the artificial heart valve. The advanced rod 2031 may be in advanced connection with a nut 14 at the proximal end of a mitral valve prosthesis 1. It should be noted that the valve delivery device 2 adopted in the present application is a medical device in the prior art, so that a specific structure will not be subject to further description herein. Further, for the cooperation with the valve delivery device 2 to advance the artificial heart valve into the ventricle from the distal end of the guide wire 322 and place it at the primary valve between the ventricle and the atrium along the guide wire 322, the implantation device of the artificial heart valve of the present application further includes a cardiac apex expansion sheath 341 and a sheath core 342. The sheath core 342 may gradually expand a puncture point at the cardiac apex to enable the cardiac apex expansion sheath 341 to arrive at the left atrium LA, and the valve delivery device 2 may implant the artificial heart valve to the primary valve through the cardiac apex expansion sheath 341.

As shown in exemplary FIGS. 11, 13, 14, and 19, by use of the above-mentioned implantation device of the artificial heart valve, the present application provides an implantation method of the artificial heart valve. The implantation method of the artificial heart valve includes: S12: forming an incision in the left chest to expose the ventricle; S14: advancing a guide wire 322, kept away from chordae tendineaes, through the atrium into the ventricle; S16: advancing a guide wire catcher into the ventricle from the incision to pull out the distal end of the guide wire 322 from the ventricle; and S18: advancing the artificial heart valve into the ventricle from the distal end of the guide wire 322 through a valve delivery device 2 and placing it at a primary valve between the ventricle and the atrium along the guide wire 322. According to the implantation method of the artificial heart valve of the present application, in a process of building a guide wire track of the artificial heart valve, the situation where the guide wire 322 passes through gaps 24 between the chordae tendineaes 21 may be effectively reduced, so that the situation that a tie rope 13 on the artificial heart valve passes through the gaps 24 between the chordae tendineaes 21 may be reduced during implantation of the artificial heart valve along the guide wire track. Thus the situation that the artificial heart valve may not be horizontally placed at the primary valve as the tie rope 13 passes through the gaps 24 between the chordae tendineaes 21 during the implantation of the artificial heart valve and the phenomenon of perivalvular leakage in the artificial heart valve after the implantation of the artificial heart valve are reduced. Meanwhile, the guide wire track of the present application may effectively reduce the damage to the chordae tendineaes 21 caused by hanging the tie rope 13 on the chordae tendineaes 21 during the implantation of the artificial heart valve. It should be noted that the atrium and the ventricle of the present application may be the left atrium LA and the left ventricle LV or the right atrium RA and the right ventricle RV. When the atrium and the ventricle are the left atrium LA and the left ventricle LV, the primary valve of the present application is a mitral valve MV. When the atrium and the ventricle are the right atrium RA and the right ventricle RV, the primary valve of the present application is a tricuspid valve WV. Further, the primary valve of the present application is not limited to the mitral valve MV or the tricuspid valve WV, it may also be other valves in the heart system, as understood by a person of ordinary skill in the art. Further, in step S14 where the guide wire 322 that passes through the atrium and the ventricle in sequence kept away from the chordae tendineaes 21 is advanced into the heart system, the guide wire 322 may be advanced into the atrium and the ventricle through a vein blood vessel or directly puncture the atrium and the ventricle in a puncturing way. An exemplary advancing method of the guide wire 322 will be described below in detail.

Figure 6:
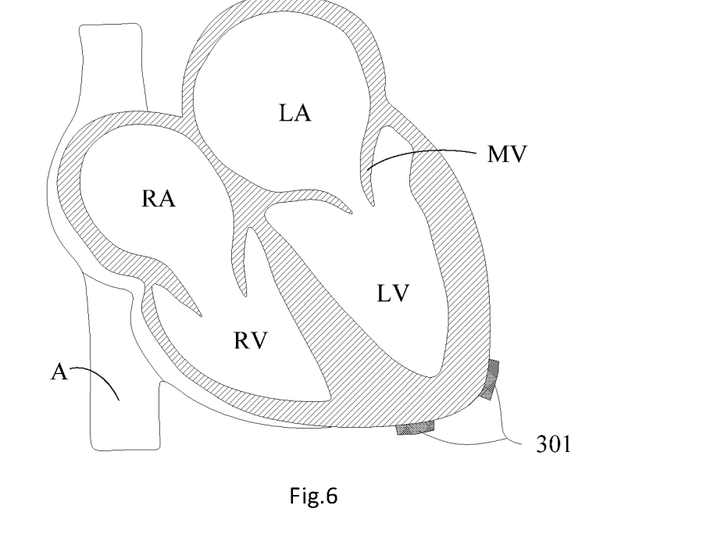
FIG. 6 is a structural schematic diagram of a heart system and an apex pouch.
Figure 7:
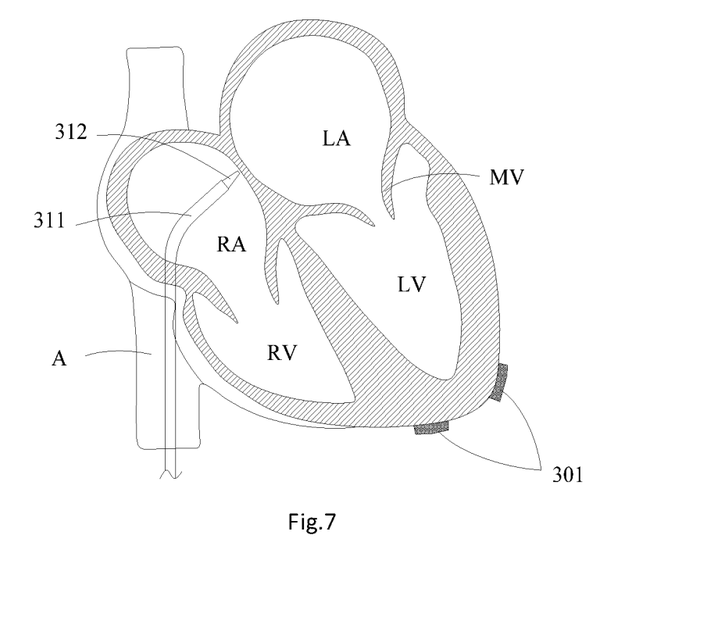
FIG. 7 is a structural schematic diagram of advancing a puncture sheath and a puncture expander through an inferior vena cava into the right atrium.
Figure 8:
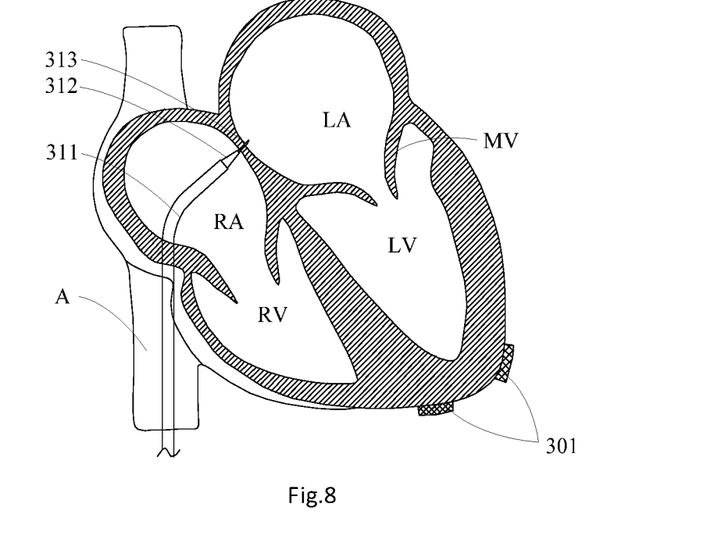
FIG. 8 is a structural schematic diagram of puncturing the atrial septum by a puncture needle in the puncture expander.
Figure 9:
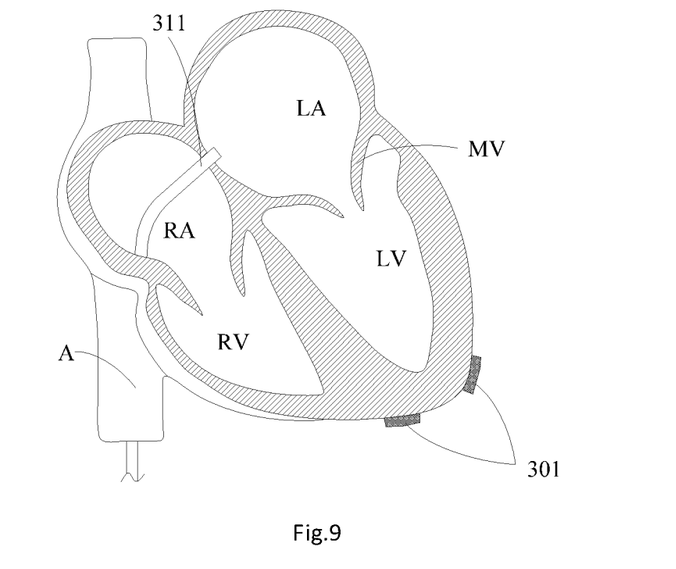
FIG. 9 is a structural schematic diagram of advancing the puncture sheath into the left atrium.
Figure 10:
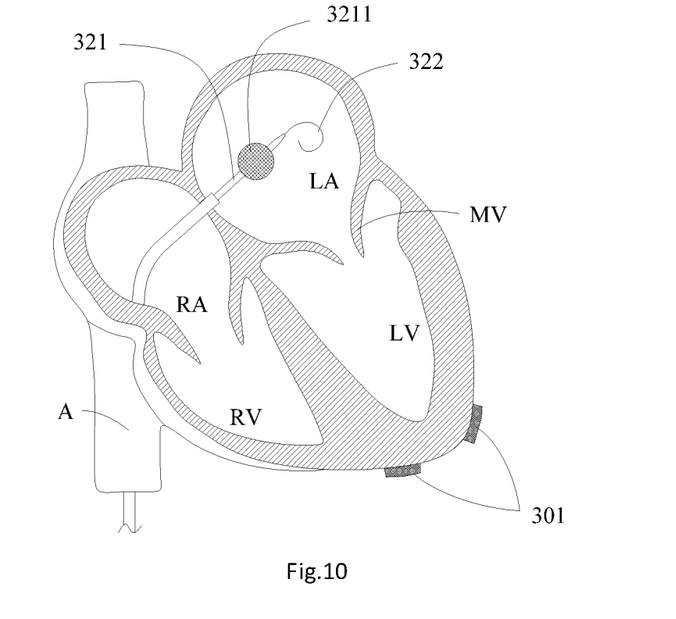
FIG. 10 is a structural schematic diagram of advancing a balloon catheter and a guide wire through the puncture sheath into the left atrium.
Figure 11:
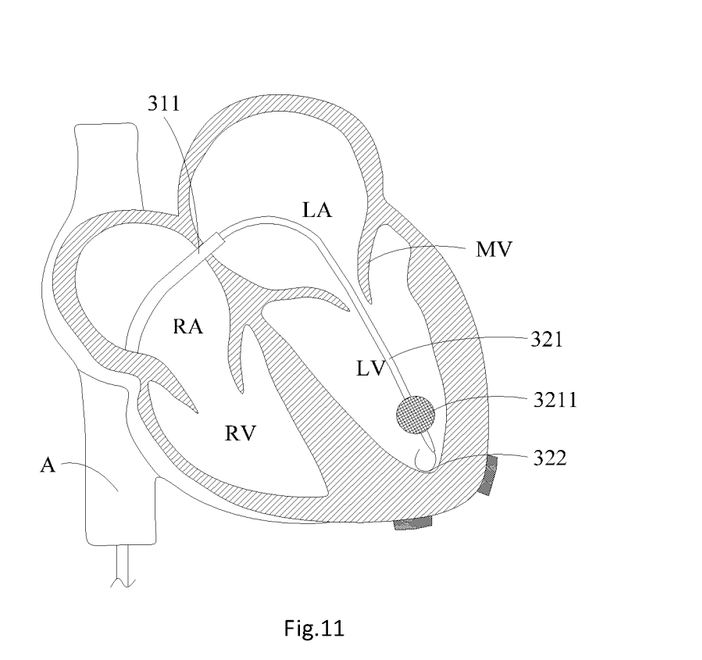
FIG. 11 is a structural schematic diagram of advancing the balloon catheter into the cardiac apex of the left ventricle.
Figure 12:
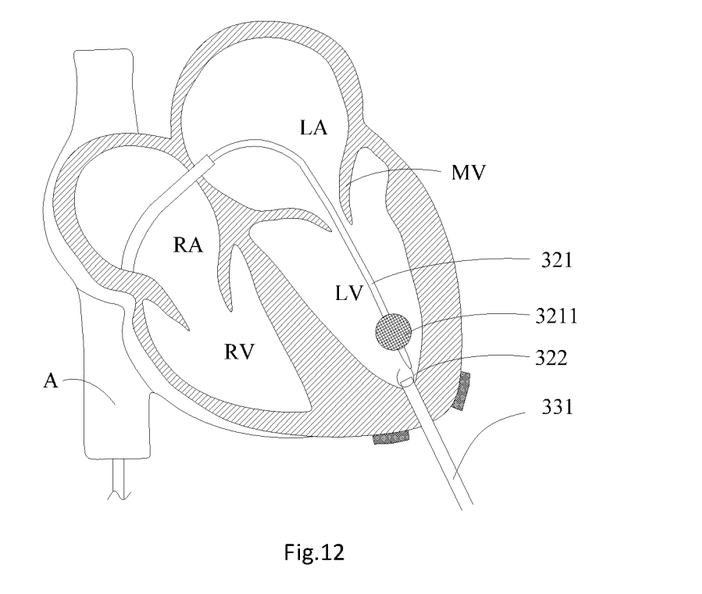
FIG. 12 is a structural schematic diagram of advancing a guide sheath into the left ventricle.
Figure 13:
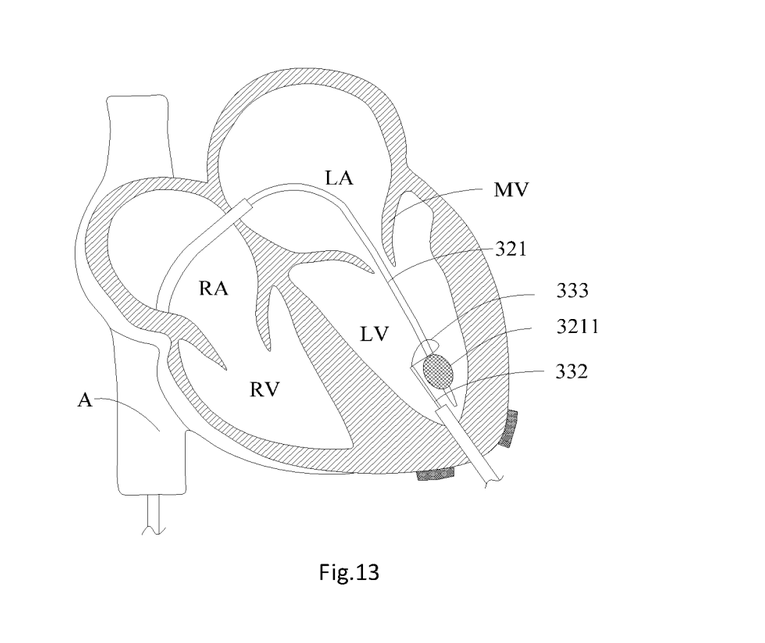
FIG. 13 is a structural schematic diagram of catching a balloon in the left ventricle by a contractible ring sleeve on a catching rod.
Figure 14:
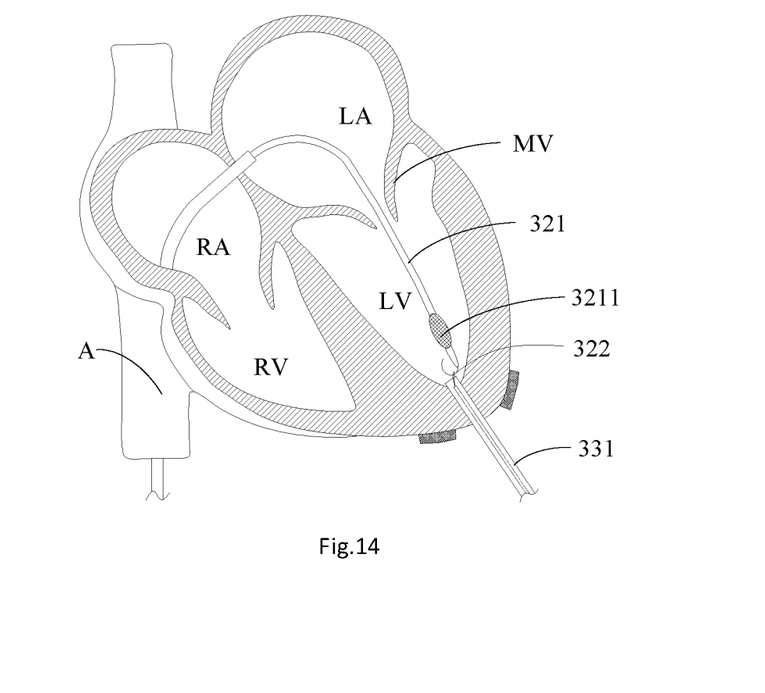
FIG. 14 is a structural schematic diagram of catching the guide wire in the left ventricle by the contractible ring sleeve on the catching rod.
Figure 15:
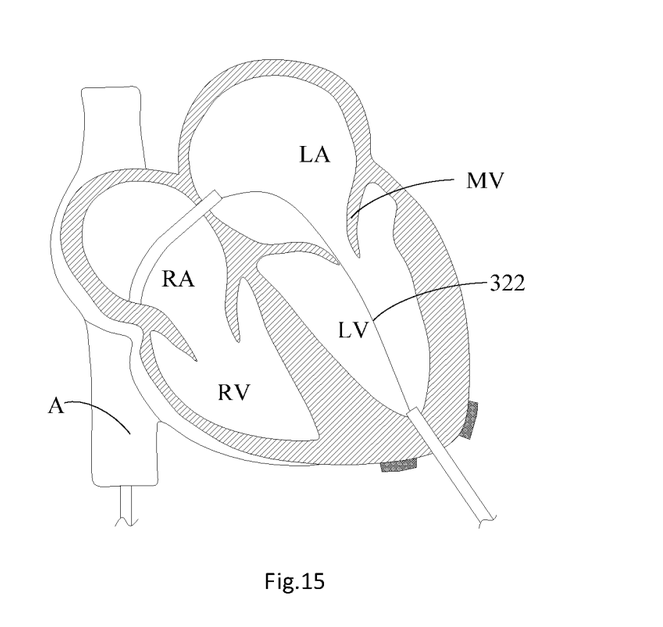
FIG. 15 is a structural schematic diagram of a guide wire track.
Figure 16:
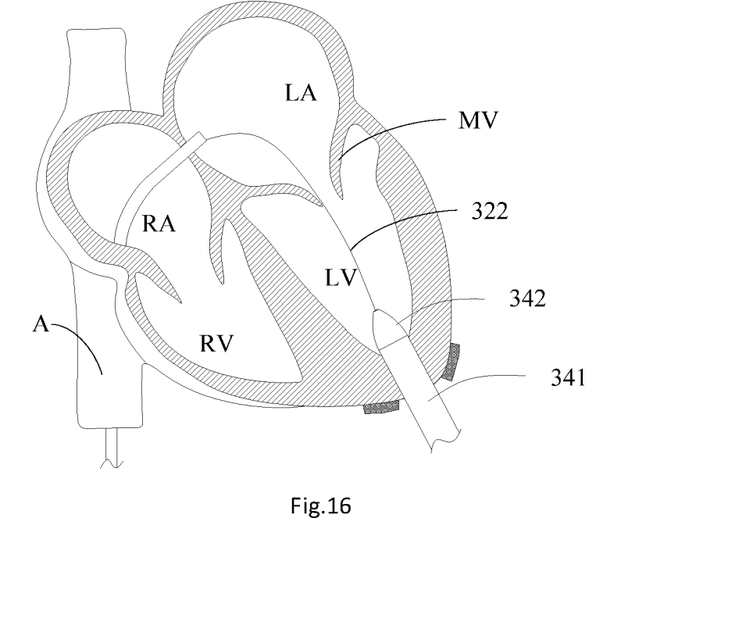
FIG. 16 is a structural schematic diagram of advancing a cardiac apex expansion sheath and a sheath core into the left ventricle.
Figure 17:
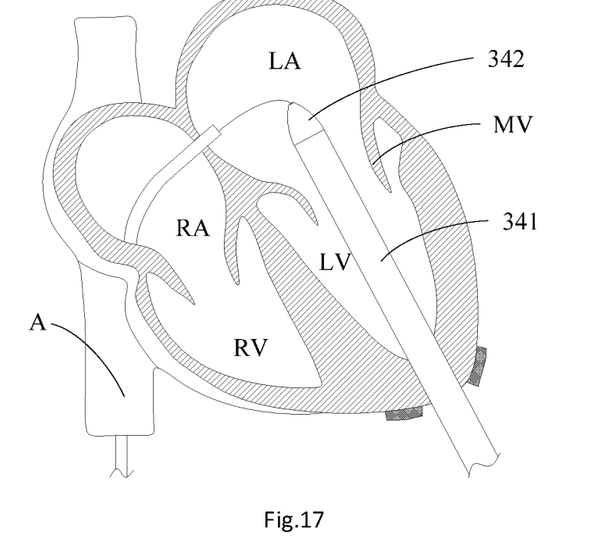
FIG. 17 is a structural schematic diagram of advancing the cardiac apex expansion sheath and the sheath core into the left atrium.
Figure 18:
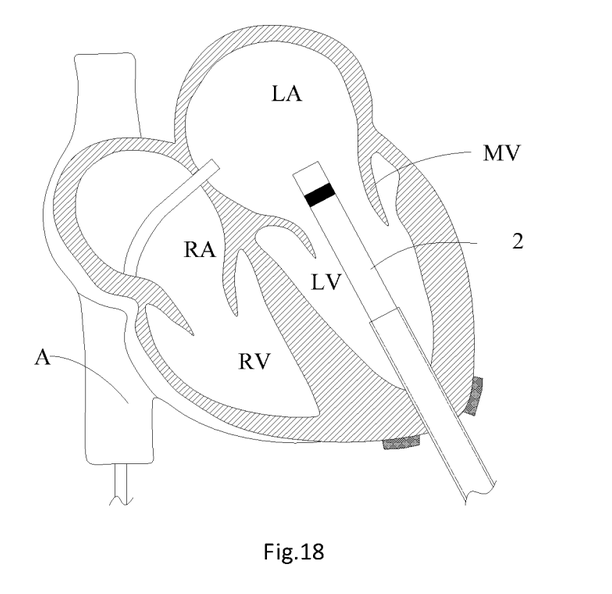
FIG. 18 is a structural schematic diagram of advancing the valve deliverer into the left atrium.
Figure 19:
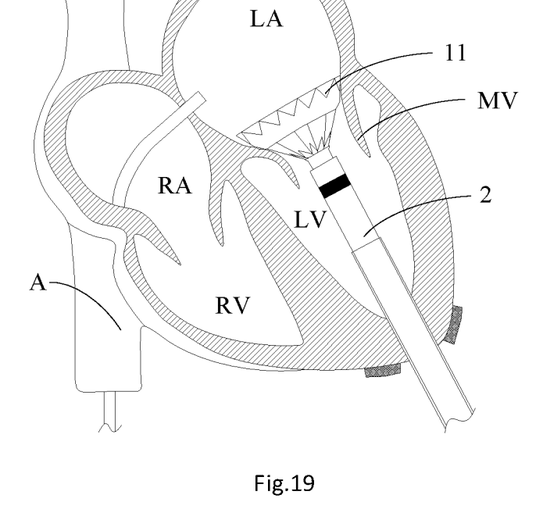
FIG. 19 is a structural schematic diagram of releasing the mitral valve prosthesis from the valve deliverer.

As shown in exemplary FIG. 6 and exemplary FIG. 12, to facilitate the description of the implantation method of the artificial heart valve, the present application is described by applying the implantation method of the artificial heart valve to the implantation operation of the mitral valve prosthesis 1. Step S12 includes that: S122: forming an incision in a gap between the fifth costa and the sixth costa of the left anterior chest, and opening the pericardium longitudinally through the incision to expose the cardiac apex of the left ventricle LV; and S124: suturing an apical pouch 301 at the cardiac apex of the left ventricle LV. In the present application, the apical pouch 301 is sutured at the cardiac apex of the left ventricle LV, so that a cardiac apex puncture needle and a guide sheath 331 may puncture the cardiac apex of the left ventricle LV through the apical pouch 301. After the surgery of the artificial heart valve is completed, the apical pouch 301 may be strained to extrude a tissue at a cardiac apex puncture hole together so as to contribute to improving the healing effect and the healing speed of the tissue at the cardiac apex puncture hole.

As shown in exemplary FIGS. 7 to 11, step S14 includes: S141: a vascular sheath puncturing an inferior vena cava A to form a puncture hole; S142: guiding a puncture sheath 311 and a puncture expander 312 into the right atrium RA through the puncture hole in the inferior vena cava A, and the puncture sheath 311 puncturing the atrial septum between the right atrium RA and the left atrium LA through a puncture needle; S143: advancing the puncture sheath 311 and the puncture expander 312 through the atrial septum into the left atrium LA, and guiding a balloon catheter 321 into the puncture sheath 311; S144: advancing the balloon catheter 321 through the inferior vena cava A and the right atrium RA into the left atrium LA; S145: filling a balloon 3211 at the distal end of the balloon catheter 321 with a contrast medium when inflated, and leading the balloon catheter 321 into the cardiac apex of the left ventricle LV through the balloon 3211 and the contrast medium along a pathway kept away from the chordae tendineaes 21; and S146: leading the guide wire 322 into the cardiac apex of the left ventricle LV through the balloon catheter 321. For example, a vascular sheath punctures the inferior vena cava A at first, and then the puncture sheath 311 and the puncture expander 312 are guided into the right atrium RA through the inferior vena cava A under the assistance of DSA (Digital Substraction Angiography); at this time, the positions of the puncture sheath 311 and the puncture expander 312 are adjusted to enable the puncture sheath 311 and the puncture expander 312 to be aligned with oval holes in the atrial septum between the right atrium RA and the left atrium LA, and then are kept unchanged, then the puncture needle 313 is pushed out from the puncture sheath 311 and the puncture expander 312 to puncture the atrial septum. After the puncturing of the atrial septum is completed, the puncture expander 312 and the puncture sheath 311 are pushed into the left atrium LA along the puncture holes in the atrial septum for angiography confirmation; and finally, the puncture expander 312 and the puncture needle 313 are withdrawn from the left atrium LA. After the puncturing of the atrial septum is completed, the puncture sheath 311 may be maintained or replaced by a head end-preshaped delivery sheath or a head end-bendable sheath. The adaptable balloon catheter 312 and the guide wire 322 having a J-shaped head end are guided into the left atrium LA through the puncture sheath 311. After the balloon catheter 321 and the guide wire 322 arrive at the left atrium LA, the balloon 3211 on the balloon catheter 321 is filled with the contrast medium. In a process that the balloon catheter 321 passes through the chordae tendineaes 21 in the left ventricle LV, the guide wire 322 is located in an inner cavity of the balloon catheter 321. After the balloon catheter 321 and the guide wire 322 arrive at the cardiac apex of the left ventricle LV, the guide wire 322 is pushed to enable the J-shaped head end to just be exposed from the balloon catheter 321. For example, the filled balloon 3211 may be spherical or elliptical and has a maximum outer diameter ranging between about 10 mm to about 20 mm, which is greater than the gaps 24 between the chordae tendineaes 21 in the left ventricle LV, so as to prevent the balloon 3211 from passing through the gaps 24 between the chordae tendineaes 21 in the subsequent operating process. Then under the assistance of the DSA, the balloon catheter 321 and the guide wire 322 are slowly pushed. In the process of pushing the balloon catheter 321 and the guide wire 322, the guide wire 322 is completely withdrawn in the balloon catheter 321, and the positions of the balloon catheter 321 and the guide wire 322 are kept relatively fixed, so that the balloon catheter 321 and guide wire 322 may arrive at the left ventricle LV after passing through the mitral valve MV from the left atrium LA as a whole. As the blood flow direction is from the left atrium LA to the left ventricle LV to an aorta, the balloon catheter 321 is guided to the left ventricle LV from the left atrium LA along the blood flow direction, and the filled balloon 3211 easily strides the mitral valve MV and gets into the left ventricle LV. In the process of pushing the balloon catheter 321 and the guide wire 322, under the assistance of the DSA, it is observed whether the balloon catheter 321 is distorted abnormally in the left ventricle LV or not or whether the pushing force is high or not. If the balloon catheter 321 is distorted abnormally (i.e., if YES), the balloon catheter 321 may be withdrawn, adjusted in angle and pushed again, and finally the balloon catheter 321 and the guide wire 322 are pushed to the cardiac apex part of the left ventricle LV. The balloon catheter 321 and the guide wire 322 are pushed along the blood flow direction, and the diameter of the balloon 3211 is greater than the gaps 24 between the chordae tendineaes 21, so that the balloon catheter 321 and the guide wire 322 do not pass through the gaps 24 between the chordae tendineaes 21 at the arrival of the cardiac apex.

As shown in exemplary FIG. 12 to FIG. 15, step S16 includes that: S161: puncturing the cardiac apex of the left ventricle LV at the apical pouch 301 with the cardiac apex puncture needle to form the puncture hole; S162: guiding the guide sheath 331 into the left ventricle LV through the puncture hole in the apical pouch 301; S163: leading the catching rod 332 and the contractible ring sleeve 333 into the left ventricle LV through the guide sheath 331; S164: advancing the guide wire catcher into the left ventricle LV from the apical pouch 301; and S165: the guide wire catcher catching the distal end of the guide wire 322 tight and then pulls out the distal end of the guide wire 322 from the left ventricle LV, wherein the distal end of the guide wire 322 is provided with the J-shaped head end. In one embodiment, step S165 includes: adjusting the size of the balloon 3211 on the balloon catheter 321 to sleeve the balloon 3211 with the contractible ring sleeve 333 through the balloon catheter 321; the guide wire 322 is pushed out of the balloon catheter 321, and the pressure of the balloon 3211 is relieved; and the contractible ring sleeve 333 is gradually tightened, and the catching rod 332 and the contractible ring sleeve 333 are slowly withdrawn till the contractible ring sleeve 333 slides to the guide wire 322, and catches the J-shaped head end of the guide wire 322 tight. For example, the cardiac apex is punctured with the cardiac apex puncture needle. After the cardiac apex puncture needle punctures the left ventricle LV, the guide sheath 331 is guided into the cardiac apex through the puncture hole. After the positional relationship between the guide sheath 331 and the wall of the left ventricle LV is adjusted through a DSA image so as to enable the guide sheath 331 to be just (or slightly) advanced into the left ventricle LV; the catching rod 332 is led into the left ventricle LV through the guide sheath 331, where the head end of the catching rod 332 is provided with the closed contractible ring sleeve 333. At this time, the size of the balloon 3211 on the balloon catheter 321 is reduced by about 10 to about 40 percent, and the guide wire 322 is withdrawn into the balloon catheter 321 at the same time; and the balloon catheter 321 and the guide wire 322 are kept steady near the cardiac apex. Then the catching rod 332 is pushed. Under the assistance of the DSA, after the contractible ring sleeve 333 at the head end of the catching rod 332 is arranged into the balloon catheter 321 in a sleeved manner, the catching rod 332 passes through the balloon 3211; then the guide wire 322 is pushed out of the balloon catheter 321, so that the J-shaped head end of the guide wire 322 is just exposed from the balloon catheter 321, and the pressure of the balloon 3211 is relieved to recover it to a compressed state; then the contractible ring sleeve 333 at the head end of the catching rod 332 is gradually tightened, and the catching rod 332 and the ring sleeve 333 are slowly withdrawn, so that the ring sleeve 333 at the head end of the catching rod 332 slides to the J-shaped head end of the guide wire 322 through the compressed balloon 3211 and the balloon catheter 321; and at this time, the ring sleeve 333 at the head end of the catching rod 332 is tightened to catch the guide wire 322 tight and finally passes through the cardiac apex of the left ventricle LV to pull the distal end of the guide wire 322 out of the heart, and the balloon catheter 321, the catching rod 332 and the contractible ring sleeve 333 are withdrawn, so as to build a guide wire track from the position outside the body to the inferior vena cava A to the right atrium RA to the left atrium LA to the left ventricle LV to the cardiac apex to the position outside the body, and the guide wire track does not pass through the gaps 24 between the chordae tendineaes 21.

As shown in exemplary FIGS. 16 to 19, step S18 includes: S182: advancing a cardiac apex expansion sheath 341 and a sheath core 342 into the left ventricle LV along the distal end of the guide wire 322 and enabling to stride the mitral valve MV to get into the left atrium LA; and S184: withdrawing the sheath core 342 from the cardiac apex expansion sheath 341, withdrawing the guide wire 322 out of the heart system, and the valve delivery device 2 delivering the artificial heart valve to the mitral valve MV through the cardiac apex expansion sheath 341. In one embodiment, step S184 includes: locating a developing ring 2011 on the outer sheath catheter 201 and the mitral valve MV on the same horizontal plane in parallel, withdrawing the cardiac apex expansion sheath 341 into the left ventricle LV, and delivering the artificial heart valve to the mitral valve MV with the valve delivery device 2. In one embodiment, the guide sheath 331 is withdrawn from the left ventricle LV; the cardiac apex expansion sheath 341 and the sheath core 342 are advanced into the left ventricle LV along the distal end of the guide wire 322; the puncture point at the cardiac apex is gradually expanded through the sheath core 342; then the distal end of the cardiac apex expansion outer sheath is delivered into the left ventricle LV under the assistance of the DSA to push the cardiac apex expansion sheath 341 and sheath core 342 as whole and enable the whole cardiac apex expansion sheath 341 and sheath core 342 to stride the mitral valve MV to get into the left atrium LA; then the sheath core 342 and the guide wire 322 are withdrawn, and the cardiac apex expansion sheath 341 is maintained in the left ventricle LV; the valve delivery device 2 is placed in the cardiac apex expansion sheath 341 and is slowly pushed to enable the distal end of an outer sheath catheter 201 of the valve delivery device 2 to pass through the mitral valve MV and place the developing ring 2011 of the outer sheath catheter 201 and the mitral valve MV in the same horizontal plane in parallel; then the cardiac apex expansion sheath 341 is withdrawn into the left ventricle LV. After the position of the cardiac apex expansion sheath 341 is confirmed, a first knob 101 on a handle assembly 10 of the valve delivery device 2 is rotated to pull back the outer sheath catheter 201 towards the proximal end, so that a valve skirt 11 of the mitral valve prosthesis 1 is unconstrained on the left atrium LA side, and a valve frame main body 12 of the mitral valve prosthesis 1 is still maintained in a cavity of a withdrawing catheter 202. At this time, the position of the mitral valve prosthesis 1 released on the left atrium LA side may be observed with a DSA image. If it is found that the release position of the mitral valve prosthesis 1 is not ideal or desired, the first knob 101 on the valve delivery device 2 may be rotated to enable the outer sheath catheter 201 in the sheath assembly 20 to move towards the distal end along the axial direction so as to re-withdraw the mitral valve prosthesis 1 into the outer sheath catheter 201. After the release position of the mitral valve prosthesis 1 is confirmed, the outer sheath catheter 201 is controlled to move towards the proximal end to release the mitral valve prosthesis 1; then a second knob 102 is rotated to enable the withdrawing catheter 202 to move towards the proximal end so as to enable the mitral valve prosthesis 1 to completely extend out of the outer sheath catheter 201 and be released; then a third knob 103 is rotated to rotate a connecting catheter 203, so that a advanced rod 2031 on the connecting catheter 203 is separated from a nut 14 on the mitral valve prosthesis 1.

Figure 20:
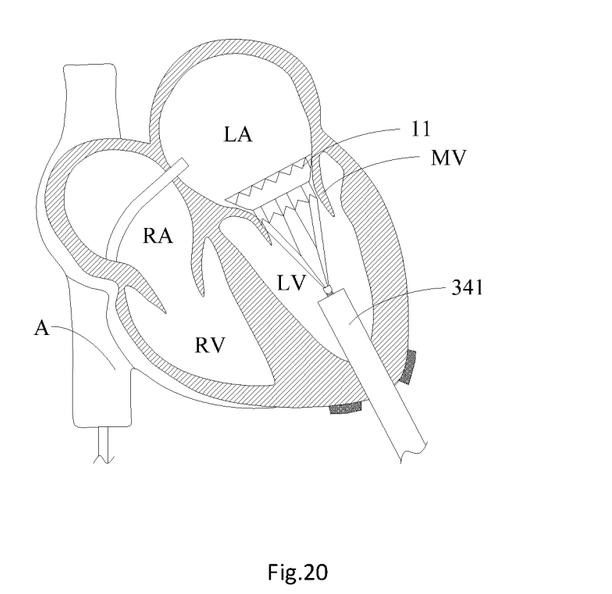
FIG. 20 is a structural schematic diagram of releasing a valve frame main body of the mitral valve prosthesis from the valve deliverer.
Figure 21:
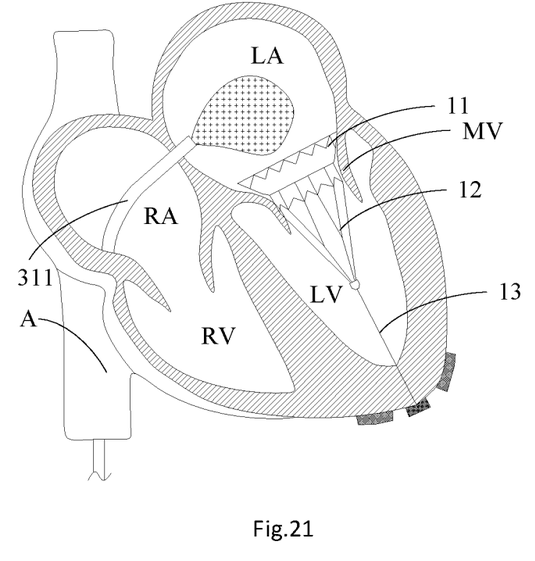
FIG. 21 is a structural schematic diagram of the mitral valve prosthesis after being implanted.

As shown in exemplary FIG. 20 and exemplary FIG. 21, after step S18, the implantation method further includes: S20: pulling the tie rope 13 at the proximal end of the artificial heart valve out of the left ventricle LV with the valve delivery device 2 and fixing it on the outer surface of the left ventricle LV. In one embodiment, after the mitral valve prosthesis 1 is implanted into the mitral valve MV of the heart, a Ruhr connecting valve 104 on the valve delivery device 2 pulls the tie rope 13 out of the left ventricle and fixes it at the cardiac apex part on the surface of the left ventricle LV, and a certain, appropriate, or predetermined pull force is applied to the tie rope 13 to enable the tie rope 13 in the left ventricle LV to be in a tightened state. At this time, the mitral valve prosthesis 1 is clung to a tissue near the opening of the mitral valve MV under the tension of the tie rope 13. After the tie rope 13 is pulled out of the left ventricle LV, the valve delivery device 2 and the cardiac apex expansion sheath 341 are withdrawn from the left ventricle LV. After the implantation operation of the mitral valve prosthesis 1 is completed, the angiography of the mitral valve prosthesis 1 in the left ventricle LV is confirmed through the puncture sheath 311; and after the angiography confirmation is completed, the puncture sheath 311 is withdrawn from the inferior vena cava A.

As shown in exemplary FIG. 21, after step S20, the implantation method further includes: S22: straining the apical pouch 301 at the cardiac apex of the left ventricle LV. In the present application, as the cardiac apex of the left ventricle LV is sutured with the apical pouch 301, the cardiac apex puncture needle and the guide sheath 331 may puncture the cardiac apex of the left ventricle LV through the apical pouch 301. After the implantation of the artificial heart valve is completed, the apical pouch 301 may be strained to extrude a tissue at the cardiac apex puncture hole together so as to contribute to improving the healing effect and the healing speed of the tissue at the cardiac apex puncture hole.

The above descriptions are merely the preferred specific implementation modes of the present application, but the protection scope of the present application is not limited to this. Changes or replacements that may be easily thought of by any persons skilled in the art within the technical scope disclosed by the present application shall all fall within the protection scope of the present application. Therefore, the protection scope of the present application shall be based on the protection scope of claims.

The invention claimed is:

1. An implantation method of an artificial heart valve, the implantation method of the artificial heart valve comprising:
S12: forming an incision in a left chest to expose a left ventricle of a heart;
S14: advancing a guide wire, the guide wire kept away from chordae tendineaes, through a left atrium into the left ventricle, the distal end of the guide wire is provided with a J-shaped head end;
wherein the step S14 is executed with a balloon catheter; the distal end of the balloon catheter is provided with a balloon; a guide wire channel and an inflating channel are arranged in the balloon catheter; and the step S14 comprises:
S144: advancing the balloon catheter through an inferior vena cava and a right atrium into a left atrium;
S145: inflating the balloon at the distal end of the balloon catheter, and leading the balloon catheter into the cardiac apex of the left ventricle by the balloon along a pathway kept away from the chordae tendineaes; and
S146: leading the guide wire into the cardiac apex of the left ventricle through the balloon catheter, the guide wire is located in the guide wire channel;
S16: advancing a guide wire catcher into the left ventricle from the incision to pull out the distal end of the guide wire from the left ventricle, the guide wire catcher comprises a catching rod, a contractible ring sleeve arranged at the distal end of the catching rod and a guide sheath arranged outside the catching rod in a sleeved manner;
wherein after the guide wire catcher is advanced into the left ventricle from the incision:
adjusting the size of the balloon on the balloon catheter by moving the contractible ring sleeve over the balloon and on the balloon catheter in a sleeved manner;
pushing the guide wire out of the balloon catheter, thereby relieving the pressure of the balloon; and
gradually tightening the contractible ring sleeve, while withdrawing the catching rod and the contractible ring sleeve till the contractible ring sleeve slides to the guide wire, the gradually tightening contractable ring sleeve catching the J-shaped head end of the guide wire to enable pulling out the distal end of the guide wire from the left ventricle; and
S18: after advancing a guide wire catcher into the left ventricle from the incision to pull out the distal end of the guide wire from the left ventricle, advancing the artificial heart valve into the left ventricle from the distal end of the guide wire with a valve delivery device, and placing the artificial heart valve at a primary valve between the left ventricle and the left atrium along the guide wire.

2. The implantation method of the artificial heart valve according to claim 1, wherein the primary valve is a mitral valve; and the step S12 comprises:
S122: forming the incision in the left chest at a gap between a fifth costa and a sixth costa of a left anterior chest, and longitudinally opening a pericardium through the incision to expose a cardiac apex of the left ventricle; and
S124: suturing an apical pouch at the cardiac apex of the left ventricle.

3. The implantation method of the artificial heart valve according to claim 2, wherein the step S145 further comprises:
filling the balloon with a contrast medium in a process of inflating the balloon, and leading the balloon catheter and the balloon into the cardiac apex of the left ventricle under the assistance of the contrast medium.

4. The implantation method of the artificial heart valve according to claim 3, wherein a puncture sheath is arranged outside the balloon catheter in a sleeved manner, and a puncture expander and a puncture needle are arranged in the puncture sheath in a sleeved manner; and the following steps are comprised between the step S124 and the step S144:

S141: puncturing the inferior vena cava with a vascular sheath to form a puncture hole;

S142: guiding the puncture sheath and the puncture expander into the right atrium through the puncture hole in the inferior vena cava, and puncturing the atrial septum between the right atrium and the left atrium with the puncture sheath by the puncture needle; and S143: advancing the puncture sheath and the puncture expander through the atrial septum into the left atrium, and guiding the balloon catheter into the puncture sheath.

5. The implantation method of the artificial heart valve according to claim 4, wherein the step S16 comprises:

S164: advancing the guide wire catcher into the left ventricle from the apical pouch; and S165: catching the distal end of the guide wire tight with the guide wire catcher and then pulling out the distal end of the guide wire from the left ventricle.

6. The implantation method of the artificial heart valve according to claim 5, the following steps are comprised between the step S144 and the step S164:

S161: puncturing the cardiac apex of the left ventricle at the apical pouch to form the puncture hole;

S162: guiding the guide sheath into the left ventricle through the puncture hole in the apical pouch; and S163: leading the catching rod and the contractible ring sleeve into the left ventricle through the guide sheath.

7. The implantation method of the artificial heart valve according to claim 1, wherein a cardiac apex expansion sheath is arranged outside the valve delivery device in a sleeved manner, and the distal end of the cardiac apex expansion sheath is provided with a sheath core; and the step S18 comprises:

S182: advancing the cardiac apex expansion sheath and the sheath core into a left ventricle along the distal end of the guide wire, and enabling the cardiac apex expansion sheath and the sheath core to stride a mitral valve to get into the left atrium; and S184: withdrawing the sheath core from the cardiac apex expansion sheath, withdrawing the guide wire out of a heart, and enabling the valve delivery device to pass through the cardiac apex expansion sheath to deliver the artificial heart valve to a mitral valve.

8. The implantation method of the artificial heart valve according to claim 7, wherein the valve delivery device comprises an outer sheath catheter, and the distal end of the outer sheath catheter is provided with a developing ring; and the step S184 comprises: locating the developing ring on the outer sheath catheter and the mitral valve on a same horizontal plane in parallel, withdrawing the cardiac apex expansion sheath into the left ventricle, and delivering the artificial heart valve to the mitral valve with the valve delivery device.

9. The implantation method of the artificial heart valve according to claim 8, wherein the proximal end of the artificial heart valve is provided with a tie rope; and after the step S18, the method further comprises:

S20: pulling the tie rope at the proximal end of the artificial heart valve out of the left ventricle with the valve delivery device, and fixing the tie rope on an outer surface of the left ventricle.

10. The implantation method of the artificial heart valve according to claim 9, wherein after the step S20, the implantation method further comprises:

S22: straining the apical pouch at the cardiac apex of the left ventricle.

* * * * *